United States Patent
Cao et al.

(10) Patent No.: US 12,232,803 B2
(45) Date of Patent: Feb. 25, 2025

(54) ALTERNATIVE PLACEMENT OF THERMAL SENSORS ON BIPOLAR ELECTRODE

(71) Applicant: Boston Scientific Scimed, Inc., Maple Grove, MN (US)

(72) Inventors: Hong Cao, Maple Grove, MN (US); Travis J. Schauer, Delano, MN (US); Henry H. Lee, Mission Viejo, CA (US); Prabodh Mathur, Laguna Niguel, CA (US); Rabih Nassif, Corona, CA (US); Andres Dandler, Newport Coast, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 288 days.

(21) Appl. No.: 17/391,435

(22) Filed: Aug. 2, 2021

(65) Prior Publication Data
US 2021/0353357 A1 Nov. 18, 2021

Related U.S. Application Data

(63) Continuation of application No. 15/874,223, filed on Jan. 18, 2018, now Pat. No. 11,116,571, which is a
(Continued)

(51) Int. Cl.
*A61B 18/14* (2006.01)
*A61B 18/00* (2006.01)

(52) U.S. Cl.
CPC .......... *A61B 18/1492* (2013.01); *A61B 2018/0016* (2013.01); *A61B 2018/0022* (2013.01);
(Continued)

(58) Field of Classification Search
CPC .......... A61B 18/1492; A61B 2018/162; A61B 2018/165; A61B 2018/1475; A61B 2018/1497; A61B 2018/00815; A61B 2018/126; A61B 2018/147; A61B 2018/00214; A61B 2018/00267; A61B 2018/1465; A61B 2018/1467; A61B 2018/00702; A61B 2018/0016; A61B 2018/0022; A61B 2018/00708; A61B 2018/00404; A61B 2018/00434;
(Continued)

(56) References Cited

U.S. PATENT DOCUMENTS 9,186,211 B2 * 11/2015 Mathur .................... A61N 1/05
2012/0071870 A1 * 3/2012 Salahieh ............ A61B 1/00181
606/33
(Continued)

*Primary Examiner* — Thomas A Giuliani
(74) *Attorney, Agent, or Firm* — Seager, Tufte & Wickhem, LLP

(57) ABSTRACT

A medical device for tissue ablation may include a catheter shaft, an expandable member disposed on or coupled to the catheter shaft, and a plurality of elongate electrode assemblies each constructed as a flexible circuit. The expandable member may be configured to shift between an unexpanded configuration and an expanded configuration. The plurality of electrode assemblies may be disposed on an outer surface of the expandable member. Each of the plurality of electrode assemblies may include a temperature sensor aligned with two or more electrodes.

20 Claims, 20 Drawing Sheets

Related U.S. Application Data continuation of application No. 14/611,755, filed on Feb. 2, 2015, now Pat. No. 9,907,609.

(60) Provisional application No. 61/935,685, filed on Feb. 4, 2014.

(52) U.S. Cl.
CPC ........... *A61B 2018/00404* (2013.01); *A61B 2018/00434* (2013.01); *A61B 2018/00511* (2013.01); *A61B 2018/00577* (2013.01); *A61B 2018/00791* (2013.01); *A61B 2018/1465* (2013.01); *A61B 2018/1467* (2013.01)

(58) Field of Classification Search
CPC .......... A61B 2018/00797; A61B 2018/00511; A61B 2018/00577; A61B 2018/00791
USPC ............ 606/41, 42, 49, 50; 607/98, 99, 101, 607/102, 113, 115, 116
See application file for complete search history.

(56) References Cited

U.S. PATENT DOCUMENTS

| | | | |
|---|---|---|---|
| 2013/0165916 A1* | 6/2013 | Mathur | A61N 1/36117 606/33 |
| 2013/0282084 A1* | 10/2013 | Mathur | A61B 18/1492 607/101 |
| 2015/0119882 A1* | 4/2015 | Cao | A61B 18/1492 606/41 |

* cited by examiner

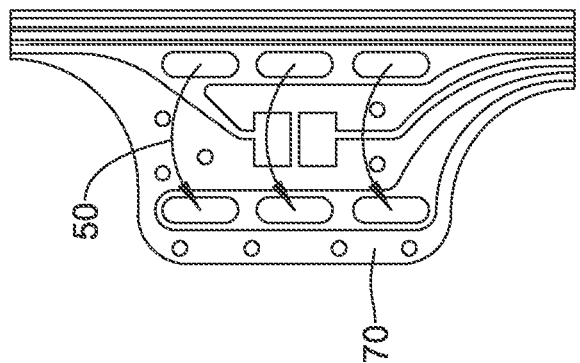
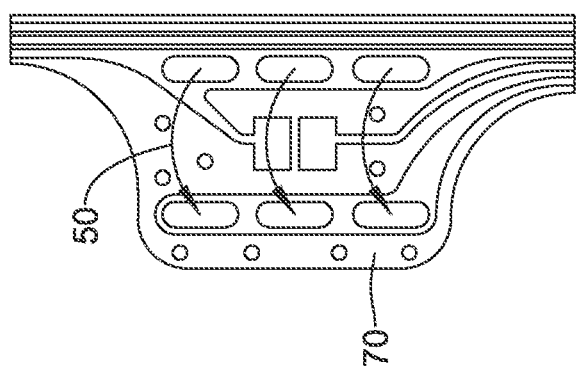
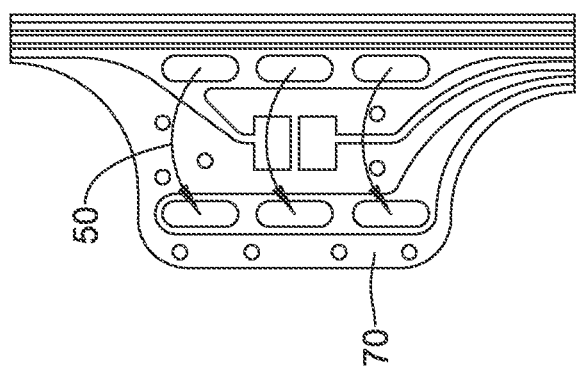
FIG. 2B
(Prior Art)

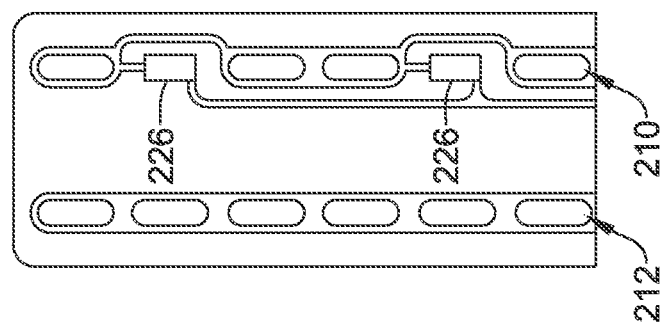

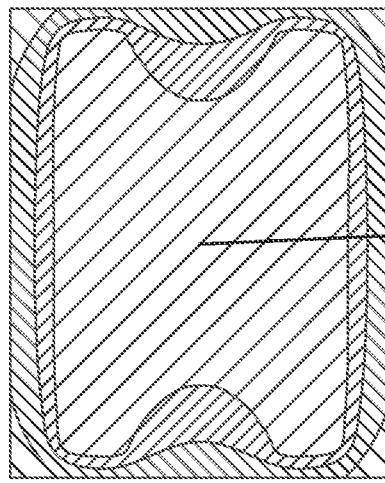
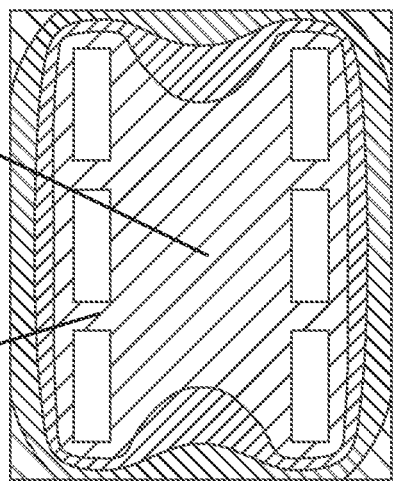
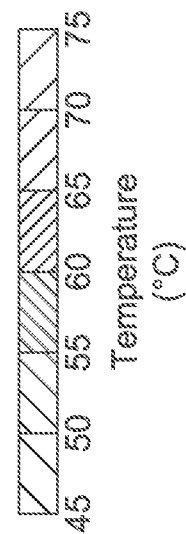
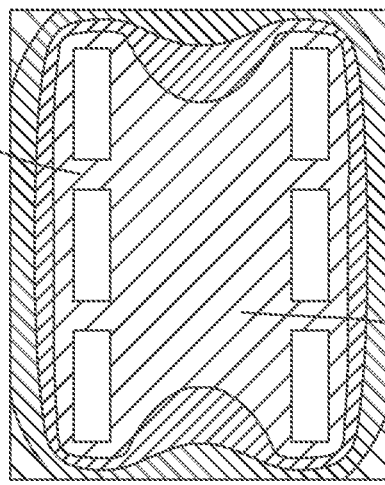

ALTERNATIVE PLACEMENT OF THERMAL SENSORS ON BIPOLAR ELECTRODE

CROSS-REFERENCE TO RELATED APPLICATIONS

This is a continuation of U.S. patent application Ser. No. 15/874,223, filed Jan. 18, 2018, now granted as U.S. Pat. No. 11,116,571, which is a continuation of application of U.S. Application Ser. No. 14,611,755, filed Feb. 2, 2015, now granted as U.S. Pat. No. 9,907,609, which claims priority under 35 U.S.C. § 119 to U.S. Provisional Application Ser. No. 61/935,685, filed Feb. 4, 2014, the disclosures of which are herein incorporated herein by reference in their entirety for all purposes.

TECHNICAL FIELD

The present disclosure pertains to medical devices, and methods for manufacturing medical devices. More particularly, the present disclosure pertains to medical devices for tissue ablation.

BACKGROUND

A wide variety of intracorporeal medical devices have been developed for medical use, for example, intravascular use. Some of these devices include guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

A medical device for tissue ablation may include a catheter shaft, an expandable balloon disposed on the catheter shaft, where the balloon may be capable of shifting between an unexpanded configuration and an expanded configuration. The medical device may include a plurality of elongate electrode assemblies each constructed as a flexible circuit, the plurality of electrode assemblies may each include a plurality of electrodes in at least first and second spaced apart arrays, the plurality of electrode assemblies may be disposed on an outer surface of the balloon. Each of the plurality of electrode assemblies may include one or more temperature sensor aligned with two or more electrodes within an array.

A medical device for tissue ablation may include a catheter shaft, an expandable member coupled to the catheter shaft, and a plurality of elongate electrode assemblies each constructed as a flexible circuit. The expandable member may be capable of shifting between an unexpanded configuration and an expanded configuration. The plurality of electrode assemblies may be disposed on an outer surface of the expandable member, and each of the plurality of electrode assemblies may include at least one temperature sensor positioned under at least one electrode.

A medical device for tissue ablation within a body passageway may include a catheter shaft having a longitudinal axis, an expandable member coupled to the catheter shaft, and a plurality of elongate electrode assemblies each constructed as a flexible circuit. The expandable member may be capable of shifting between an unexpanded configuration and an expanded configuration, and the plurality of electrode assemblies may be bonded to an outer surface of the expandable member. Each of the plurality of electrode assemblies may include a plurality of active electrodes, a plurality of ground electrodes, and one or more temperature sensor. The temperature sensor may be linearly aligned with the plurality of ground electrodes.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which:

FIGS. 2A, 2B, and 3 are partial top views of prior art electrode assemblies;

FIGS. 10A, 10B, 11, 12, and 13 are partial top views of exemplary electrode assemblies;

FIGS. 15A, 15B, and 15C are temperature profiles taken through cross-sections A-A, B-B, and C-C, respectively, of the assembly of FIG. 14.

Figure 1:
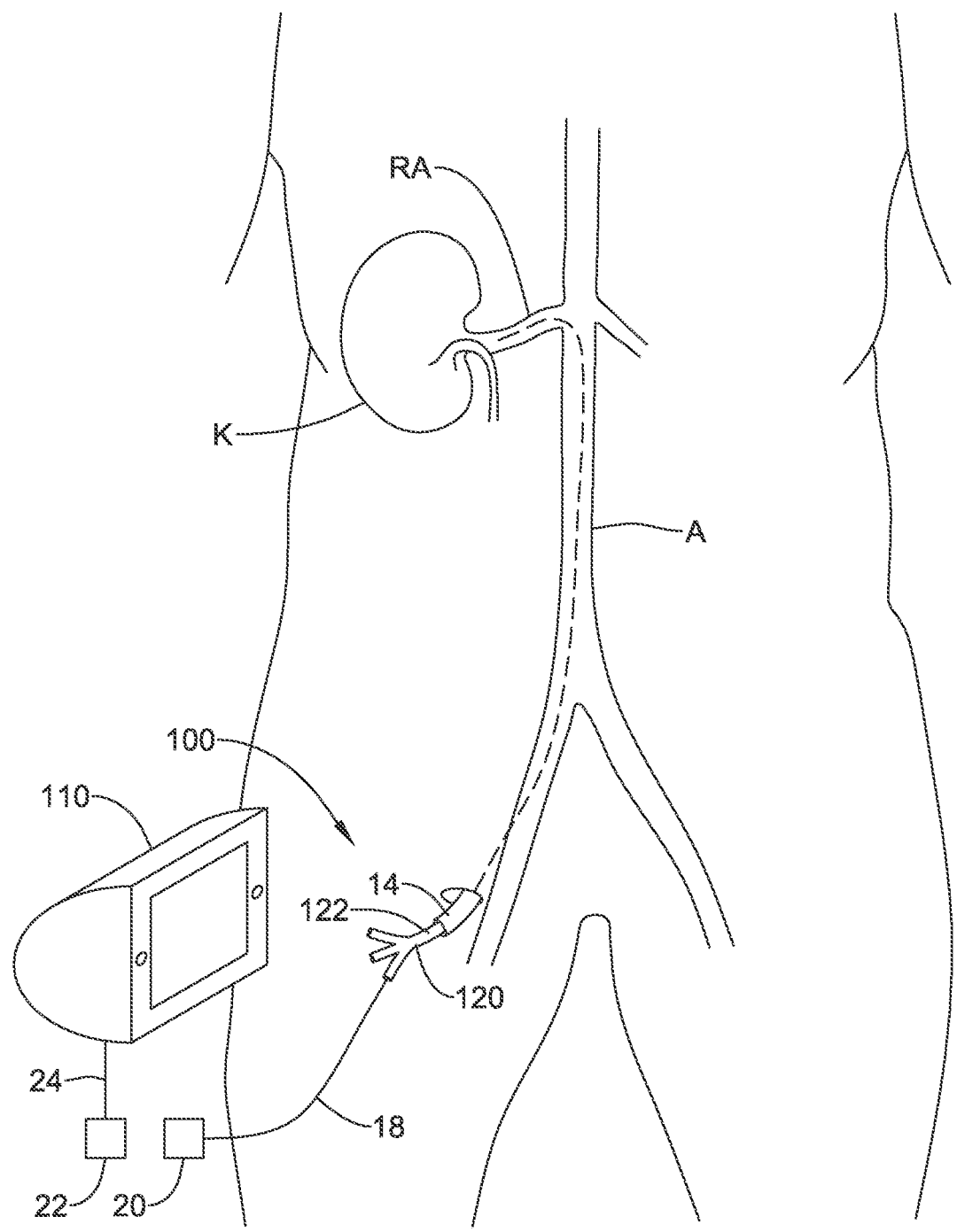
FIG. 1 is a schematic view of an example tissue ablation device.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangable with each other to form other additional embodiments or to complement and/or enrich the described embodiment(s), as would be understood by one of ordinary skill in the art.

Certain treatments are aimed at tissue ablation. In some examples, tissue ablation may include the temporary or permanent interruption or modification of select nerve function. In some embodiments, the nerves may be sympathetic nerves. One example treatment is renal nerve ablation, which is sometimes used to treat conditions such as or related to hypertension, congestive heart failure, diabetes, or other conditions impacted by high blood pressure or salt retention. The kidneys produce a sympathetic response, which may increase the undesired retention of water and/or sodium. The result of the sympathetic response, for example, may be an increase in blood pressure. Ablating some of the nerves running to the kidneys (e.g., disposed adjacent to or otherwise along the renal arteries) may reduce or eliminate this sympathetic response, which may provide a corresponding reduction in the associated undesired symptoms (e.g., a reduction in blood pressure).

Some embodiments of the present disclosure relate to a power generating and control apparatus, often for the treatment of targeted tissue in order to achieve a therapeutic effect. In some embodiments, the target tissue is tissue containing or proximate to nerves. In other embodiments, the target tissue is sympathetic nerves, including, for example, sympathetic nerves disposed adjacent to blood vessels. In still other embodiments the target tissue is luminal tissue, which may further comprise diseased tissue such as that found in arterial disease.

In some embodiments of the present disclosure, the ability to deliver energy in a targeted dosage may be used for nerve tissue in order to achieve beneficial biologic responses. For example, chronic pain, urologic dysfunction, hypertension, and a wide variety of other persistent conditions are known to be affected through the operation of nervous tissue. For example, it is known that chronic hypertension that may not be responsive to medication may be improved or eliminated by disabling excessive nerve activity proximate to the renal arteries. It is also known that nervous tissue does not naturally possess regenerative characteristics. Therefore it may be possible to beneficially affect excessive nerve activity by disrupting the conductive pathway of the nervous tissue. When disrupting nerve conductive pathways, it is particularly advantageous to avoid damage to neighboring nerves or organ tissue. The ability to direct and control energy dosage is well-suited to the treatment of nerve tissue. Whether in a heating or ablating energy dosage, the precise control of energy delivery as described and disclosed herein may be directed to the nerve tissue. Moreover, directed application of energy may suffice to target a nerve without the need to be in exact contact, as would be required when using a typical ablation probe. For example, eccentric heating may be applied at a temperature high enough to denature nerve tissue without causing ablation and without requiring the piercing of luminal tissue. However, it may also be desirable to configure the energy delivery surface of the present disclosure to pierce tissue and deliver ablating energy similar to an ablation probe with the exact energy dosage being controlled by a power control and generation apparatus.

In some embodiments, efficacy of the denervation treatment can be assessed by measurement before, during, and/or after the treatment to tailor one or more parameters of the treatment to the particular patient or to identify the need for additional treatments. For instance, a denervation system may include functionality for assessing whether a treatment has caused or is causing a reduction in neural activity in a target or proximate tissue, which may provide feedback for adjusting parameters of the treatment or indicate the necessity for additional treatments.

Many of the devices and methods described herein are discussed relative to renal nerve ablation and/or modulation. However, it is contemplated that the devices and methods may be used in other treatment locations and/or applications where sympathetic nerve modulation and/or other tissue modulation including heating, activation, blocking, disrupting, or ablation are desired, such as, but not limited to: blood vessels, urinary vessels, or in other tissues via trocar and cannula access. For example, the devices and methods described herein can be applied to hyperplastic tissue ablation, cardiac ablation, pain management, pulmonary vein isolation, pulmonary vein ablation, tumor ablation, benign prostatic hyperplasia therapy, nerve excitation or blocking or ablation, modulation of muscle activity, hyperthermia or other warming of tissues, etc. The disclosed methods and apparatus can be applied to any relevant medical procedure, involving both human and non-human subjects. The term modulation refers to ablation and other techniques that may alter the function of affected nerves and other tissue.

FIG. 1 is a schematic view of an example sympathetic nerve ablation system 100. System 100 may include a sympathetic nerve ablation device 120. Sympathetic nerve ablation device 120 may be used to ablate nerves (e.g., renal nerves) disposed adjacent to the kidney K (e.g., renal nerves disposed about a renal artery RA). In use, sympathetic nerve ablation device 120 may be advanced through a blood vessel such as the aorta A to a position within the renal artery RA. This may include advancing sympathetic nerve ablation device 120 through a guide sheath or catheter 14. When positioned as desired, sympathetic nerve ablation device 120 may be activated to activate one or more electrodes (not shown). This may include operatively coupling sympathetic nerve ablation device 120 to a control unit 110, which may include an RF generator, so as to supply the desired activation energy to the electrodes. For example, sympathetic nerve ablation device 120 may include a wire or conductive member 18 with a first connector 20 that can be connected to a second connector 22 on the control unit 110 and/or a wire 24 coupled to the control unit 110. In at least some embodiments, the control unit 110 may also be utilized to supply/receive the appropriate electrical energy and/or signal to activate one or more sensors disposed at or near a distal end of sympathetic nerve ablation device 120. When suitably activated, the one or more electrodes may be capable of ablating tissue (e.g., sympathetic nerves) as described below and the one or more sensors may be used to detect desired physical and/or biological parameters.

The sympathetic nerve ablation device 120 may include an elongate tubular member or catheter shaft 122. In some embodiments, the elongate tubular member or catheter shaft 122 may be configured to be slidingly advanced over a guidewire or other elongate medical device to a target site. In some embodiments, the elongate tubular member or catheter shaft 122 may be configured to be slidingly advanced within a guide sheath or catheter 14 to a target site. In some embodiments, the elongate tubular member or catheter shaft 122 may be configured to be advanced to a target site over a guidewire, within a guide sheath or catheter 14, or a combination thereof. An expandable member 130 may be disposed at, on, about, or near a distal region of the elongate tubular member or catheter shaft 122. In some embodiments, the expandable member 130 may be a compliant or a non-compliant balloon. In some embodiments, the expandable member 130 may be capable of shifting between an unexpanded configuration and an expanded configuration.

The use of medical devices that include a balloon with one or more electrode assemblies coupled thereto, for example as described herein, may be desirable. In some instances, however, the electrode assemblies may include relatively stiff and/or bulky materials or elements. Accordingly, when the balloon is deflated following a treatment procedure, the electrode assembly may tend to flatten and/or widen out. When so configured, the one or more electrode assemblies, and/or components or edges thereof, might catch on the edge of a guide catheter when proximally retracting the medical device (e.g., including the affixed electrode assemblies) into the guide catheter. Disclosed herein are medical devices that include structural features that may reduce the size of an electrode assembly and the likelihood of an electrode assembly or other structures of the medical device "catching" on the end of a guide catheter (or other device) when being retracted, for example, into the guide catheter, thus resulting in reduced withdrawal forces.

Figure 2A:
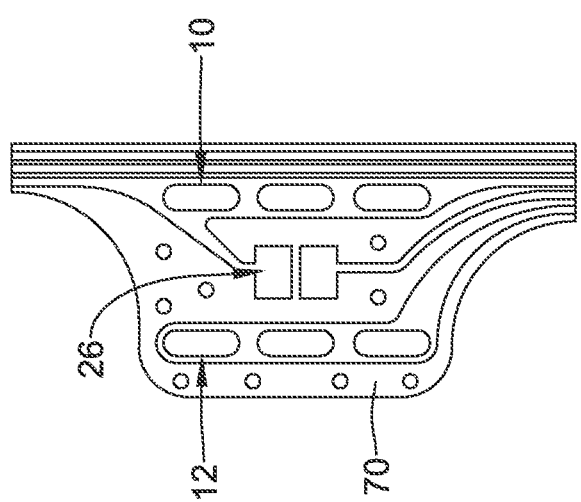

The electrode assemblies may be arranged on the expandable member and each assembly may include one or more of each of a ground electrode 10, a positive electrode 12, and a temperature sensor or thermistor 26. Some prior art electrode pair designs consisted of an electrode pad 70 having a plurality of ground electrodes 10 spaced a few millimeters apart from a plurality of positive electrodes 12, with a thermistor 26 placed in between the electrodes, as shown in FIG. 2A. This allows for accurate temperature sensing when individual electrodes are activated, creating consistent lesions. Each individual electrode pair may be activated individually, resulting in staggered treatment around the vessel. When the electrode assemblies are placed on a balloon catheter, they may be wired to individually activate around each thermistor, as shown in FIG. 2B.

Figure 3:
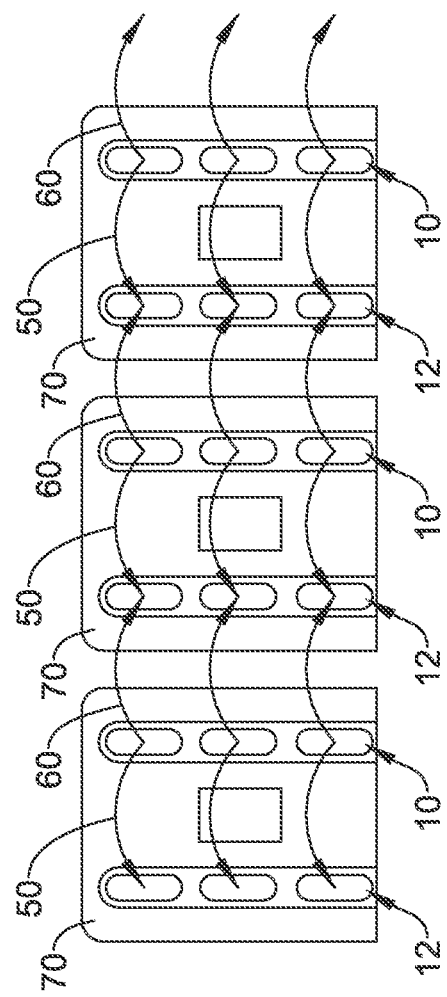

In other applications, more complete and circumferential treatment may be desired. In such applications, the electrode pairs may be arranged to fire within pairs, indicated by arrows 50, and in between pairs, indicated by arrows 60. See FIG. 3. In this scenario, the in between pairs of electrodes do not have thermistors to monitor temperature during activation.

Figure 4:
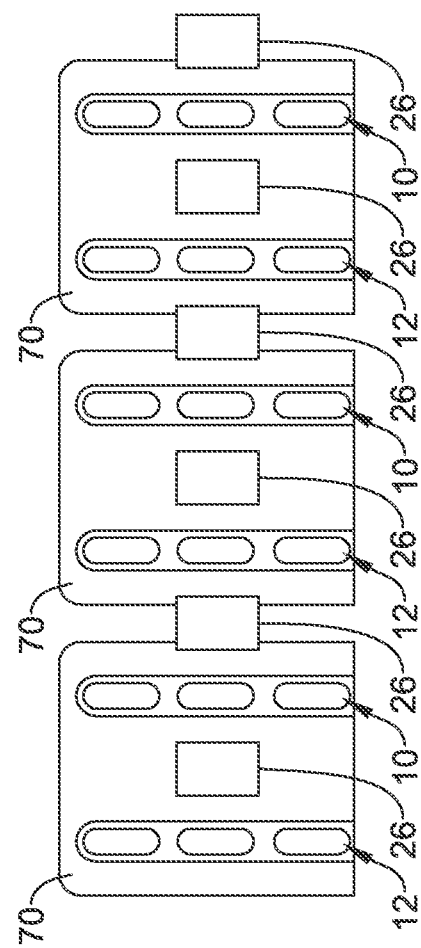
FIG. 4 is a partial top view of an exemplary electrode assembly.

In order to monitor the temperature of the in-between electrode pairs, additional thermistors 26 may be placed between the electrode pads 70, as shown in FIG. 4. However, this arrangement requires doubling the number of thermistors, which requires additional surface area on the balloon, may increase the stiffness and profile of the balloon, and requires additional electrical connections to complete the circuit for the additional thermistors. The thermistor may be the largest component of the electrode assembly. For example, a thermistor may be 0.02 inches (0.0508 centimeter) by 0.04 inches (0.1016 centimeter) and 0.006 inches (0.01524 centimeter) thick. When placed between the electrodes, the thermistor may increase the circuit profile and circuit area/mass. This structure may also make the expandable member difficult to fold, requiring a larger catheter or sheath.

In some embodiments, an off-center placement of the temperature sensor on a bipolar electrode structure may reduce the flexible circuit profile and improve balloon foldability, allowing the balloon to pass through a smaller sheath or catheter. Moving the temperature sensor off center, or in line with the electrodes may allow the expandable member to fold along the center of the two rows of electrodes without breaking the temperature sensors. During retraction of the balloon, the temperature sensor may be pulled back with the spine of the flexible circuit where the electrodes are disposed. The middle part between the two rows of electrodes is easier to fold. This structure may allow the device to be inserted and withdrawn through a smaller sheath or catheter.

Figure 5:
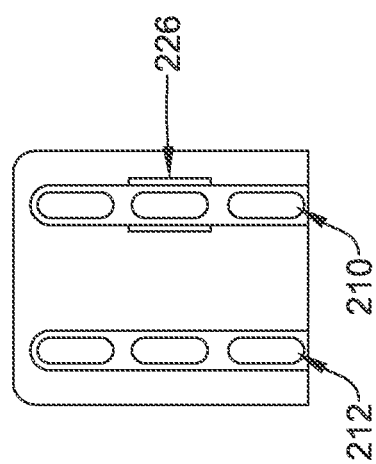
FIG. 5 is a partial top view of an exemplary electrode assembly.
Figure 6A:
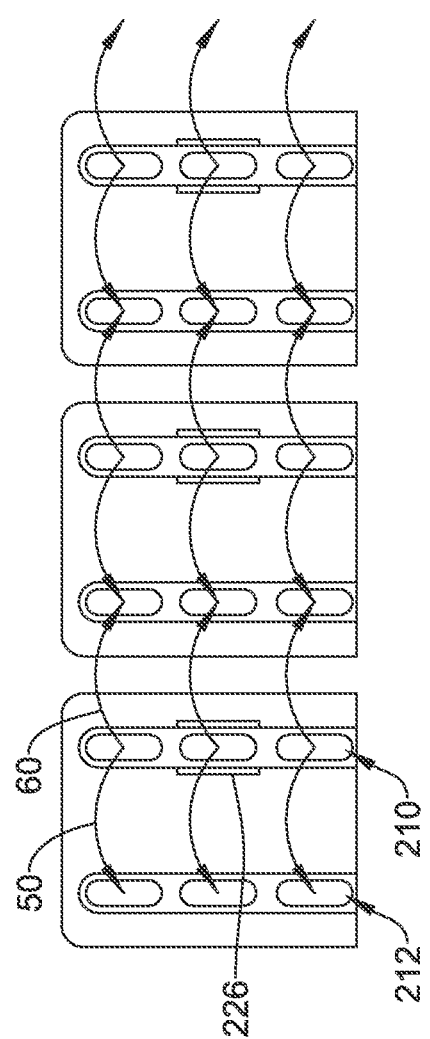
FIGS. 6A and 6B are top views of exemplary electrode assemblies.

An example temperature sensor placement is shown in FIG. 5, which provides full temperature monitoring for both within pair and in-between pair electrode activation without increasing the number of temperature sensors. The temperature sensor 226, such as a thermistor, is placed under the ground electrode 210, as shown in FIG. 5. A layer of insulation material, such as polyimide, may be placed between the ground electrode 210 and the temperature sensor 226. In this arrangement, each temperature sensor 226 may monitor the temperature of within pair electrode activation 50 and in-between pair electrode activation 60, as shown in FIG. 6A. The firing frequency and sequence may be controlled by the generator hardware and software, which may optimize temperature accuracy and may reduce the amount of cross-talk during electrode activation and temperature sensing. In some embodiments, longer balloons may be desired. The electrode assemblies 140 may be lengthened and additional electrodes 222, including both ground electrodes 210 and active positive electrodes 212, and temperature sensors 226 may be added in arrays extending along the length of the electrode to monitor the temperature across the entire length. See FIG. 6B. The electrode arrays may be oriented parallel to each other or at an angle to each other, and may be spaced apart. In some embodiments, the area 145 of the electrode assembly between the arrays of electrodes 210, 212 is devoid of circuitry. This area 145 devoid of circuitry may aid in folding the electrode assemblies.

Each electrode assembly 140 may include a plurality of discrete conductive traces layered on top of a base layer 202. The plurality of discrete conductive traces may include a ground electrode trace 210, an active or positive electrode trace 212, and a temperature sensor trace 214. The ground electrode trace 210 may include an elongated ground electrode support 216, and the active electrode trace 212 may include an elongated active electrode support 217. The electrode supports 216, 217 may taper down in width at their proximal ends to provide a desired amount of flexibility, however, this is not required. Generally, the curvature of the traces where necking is shown may be optimized to reduce balloon recapture forces and to reduce the potential for any snagging that sharper contours may present. The shape and position of the traces may also be optimized to provide dimensional stability to the electrode assembly 140 as a whole, so as to prevent distortion during deployment and use.

Figure 17:
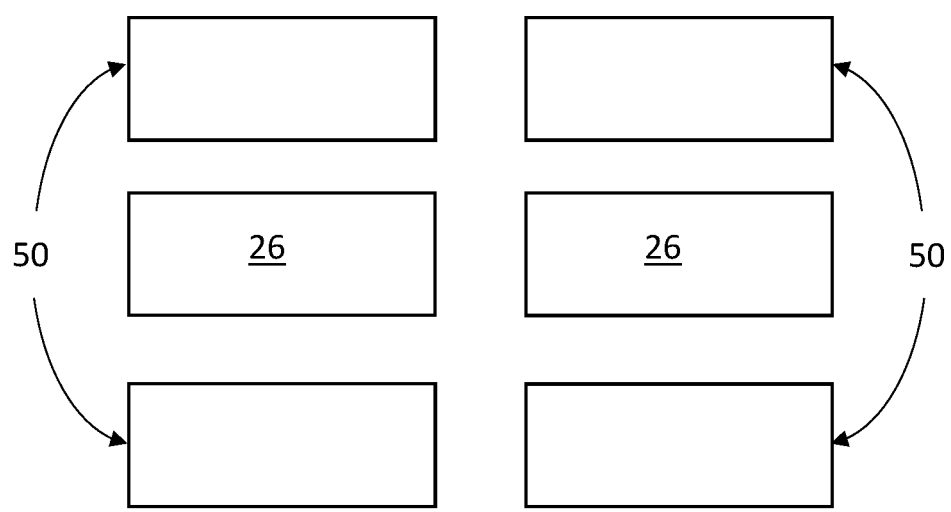
FIG. 17 is a schematic representation of an electrode assembly having a plurality of electrode pairs, wherein a thermistor is disposed between each electrode pair of the plurality of electrode pairs, according to an embodiment of the present disclosure.

In some embodiments, as represented schematically in FIG. 17, an electrode assembly may be provided having a plurality of electrode pairs, in which a thermistor 26 is disposed between each electrode pair 50 of the plurality of electrode pairs.

Figure 6B:
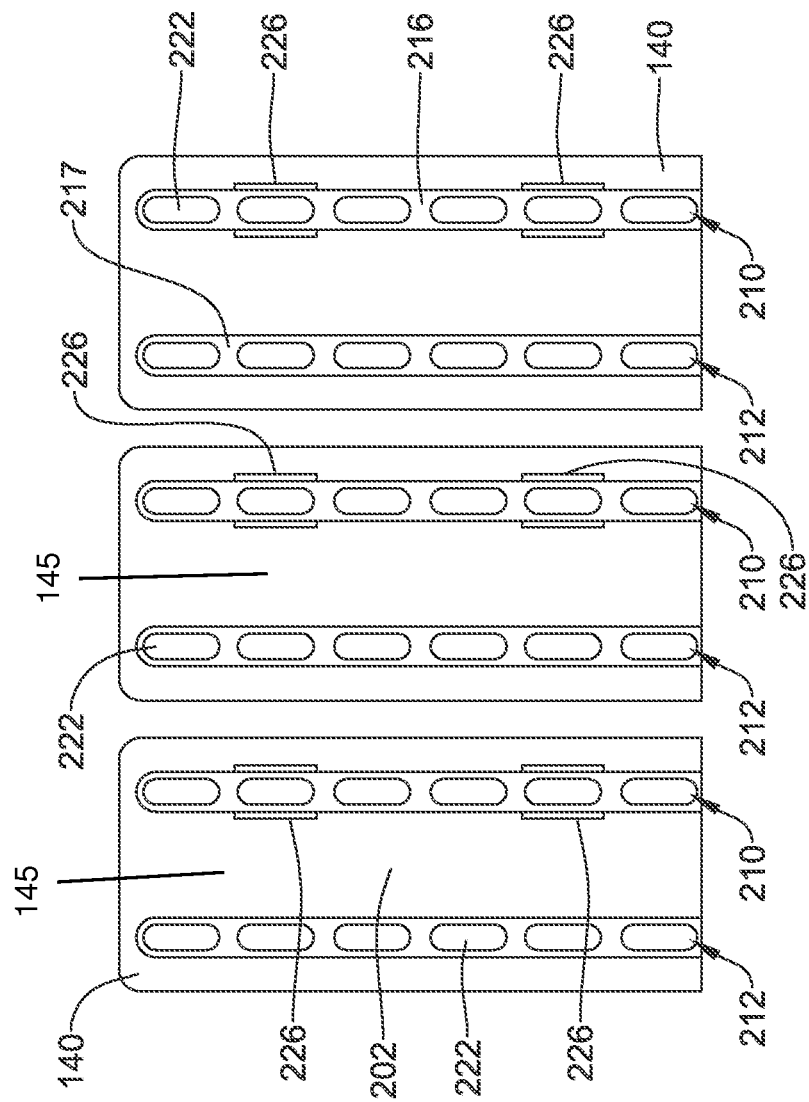
Figure 7:
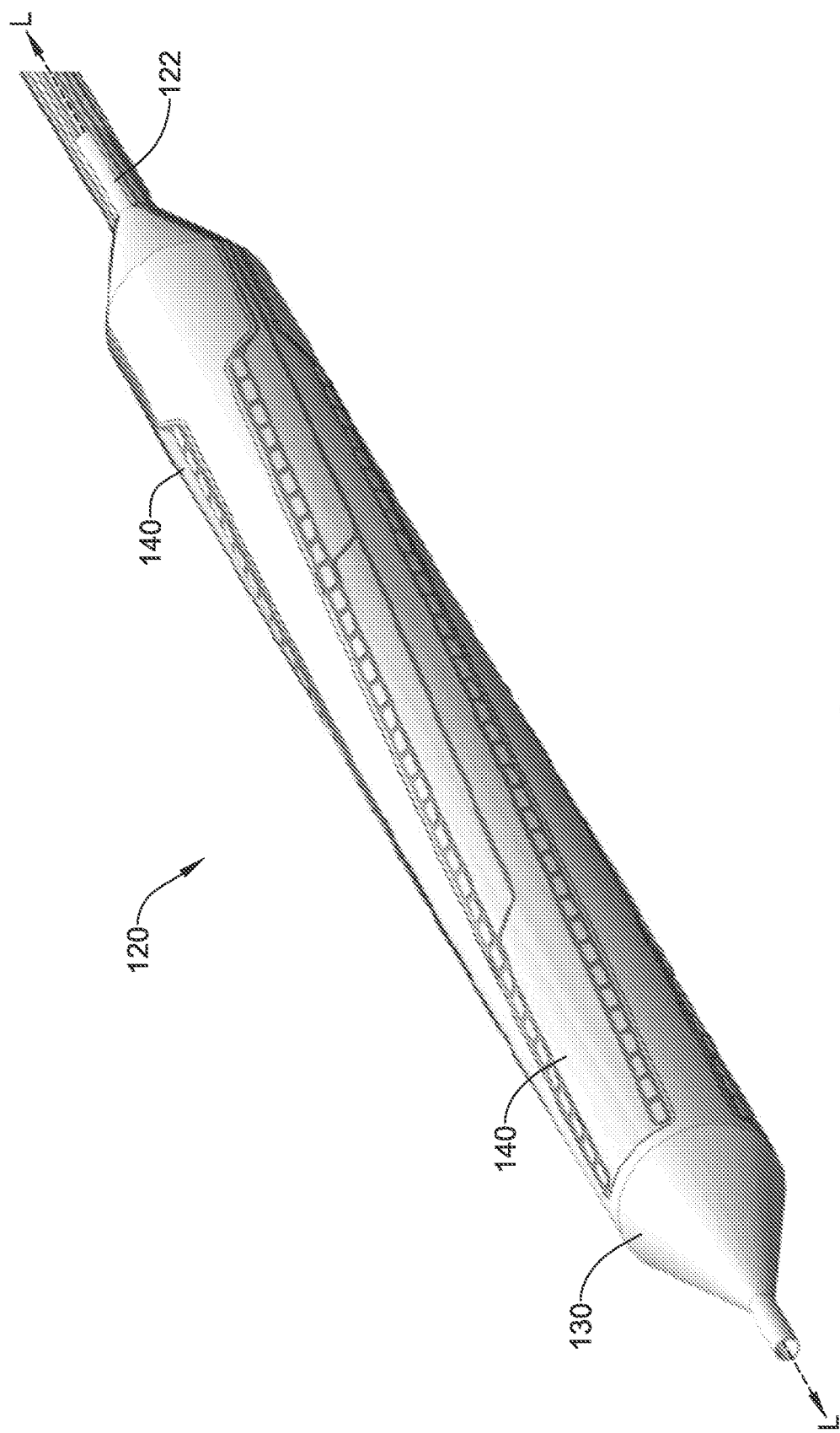
FIG. 7 is a perspective view of an exemplary expandable member of a tissue ablation device.
Figure 8:
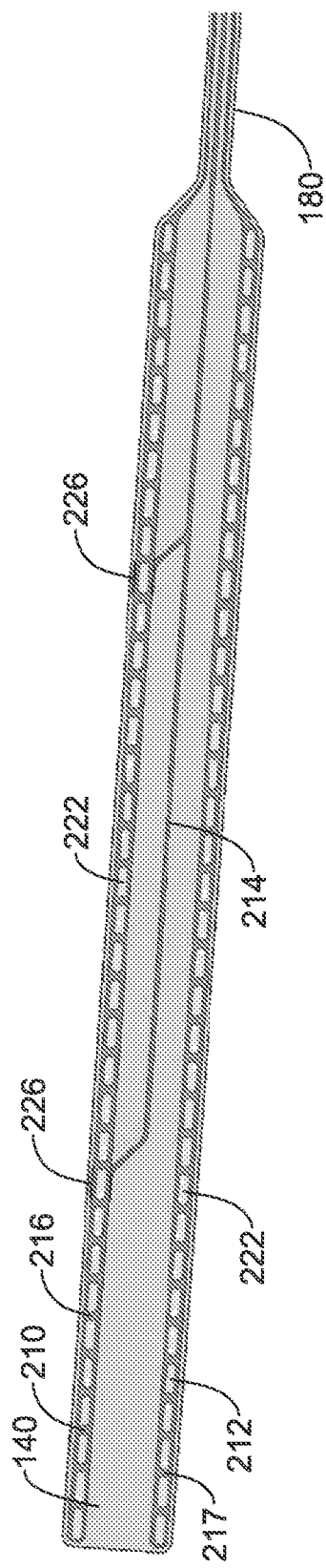
FIG. 8 is a top view of a portion of an exemplary electrode assembly.
Figure 11:
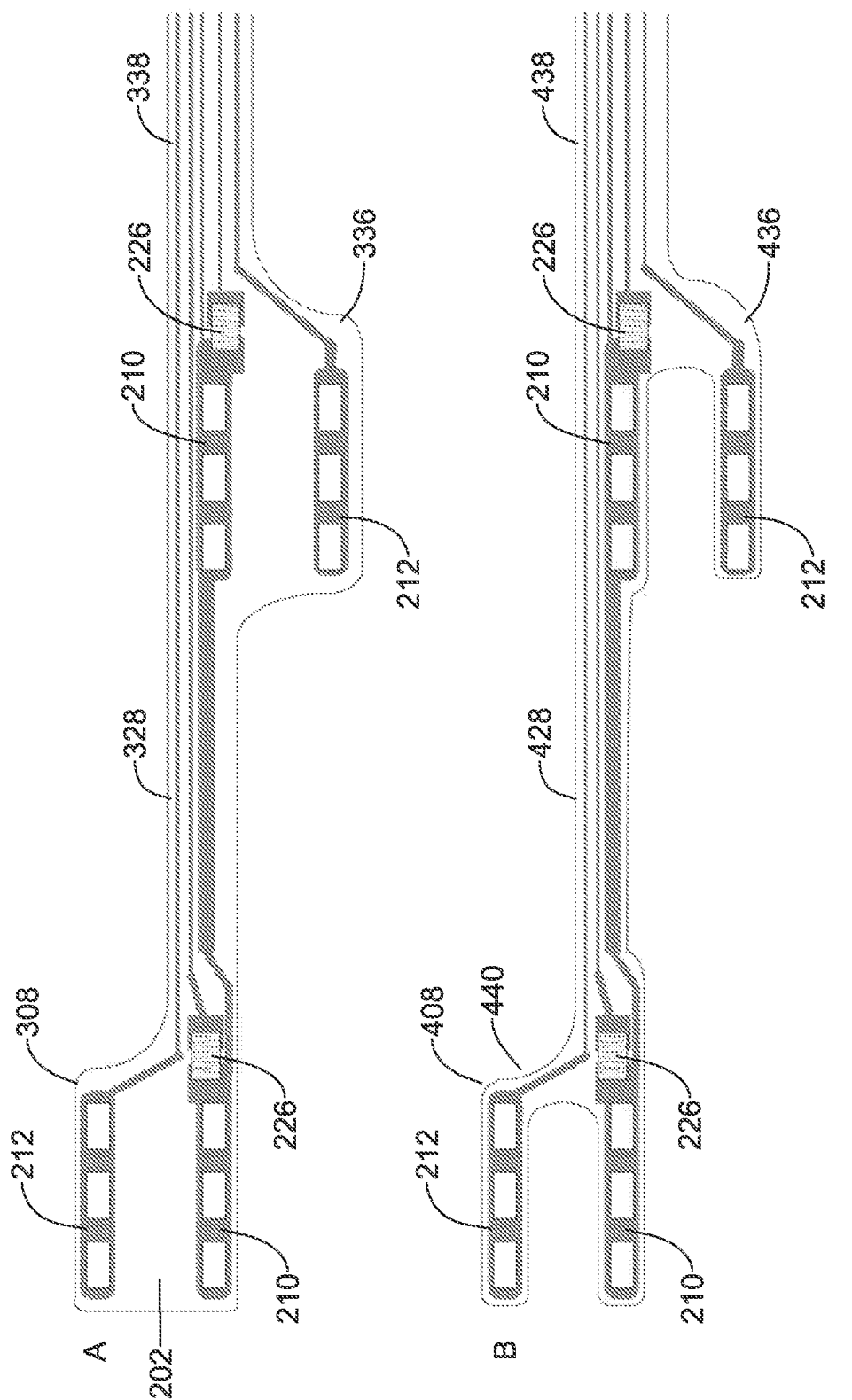
Figure 12:
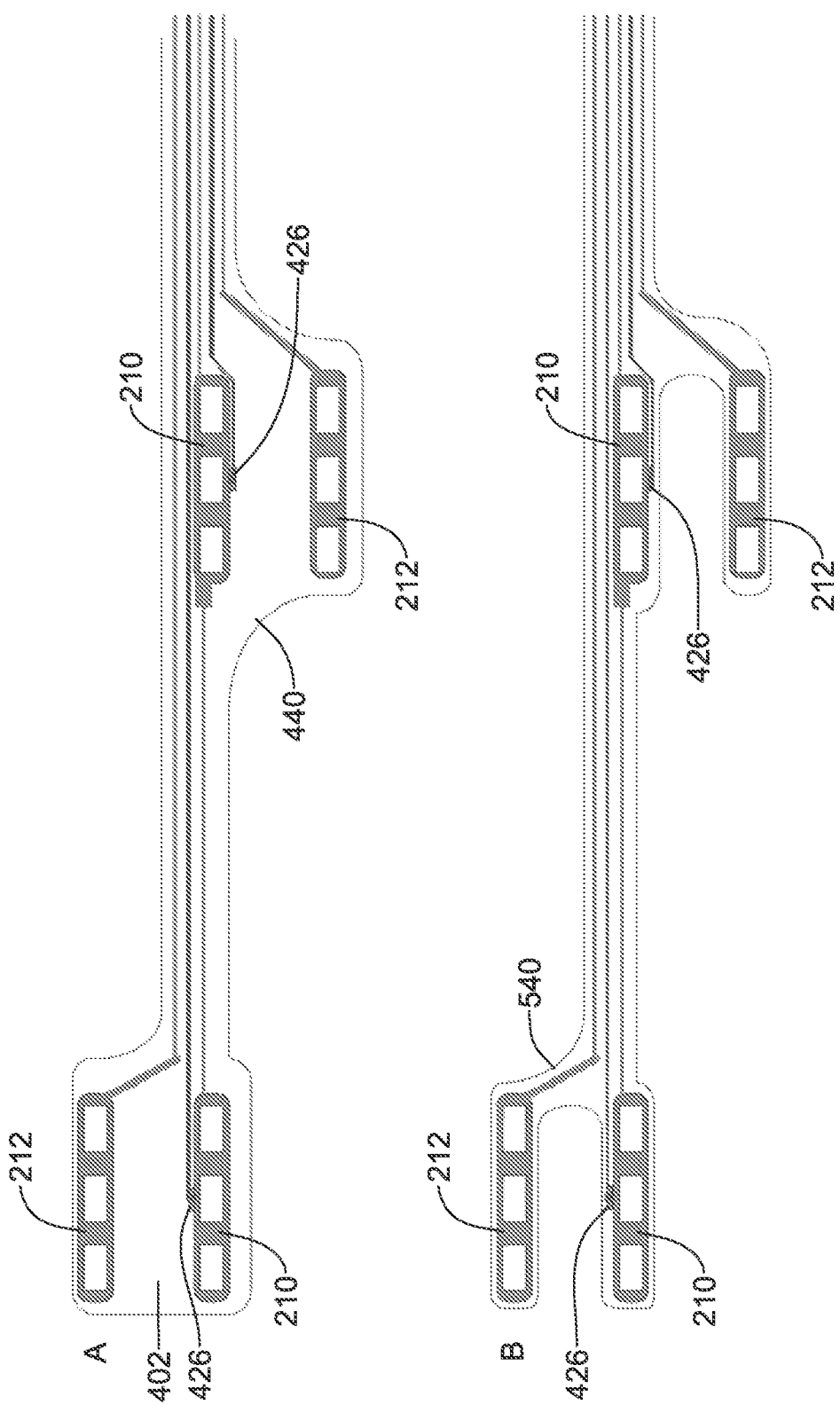
Figure 13:
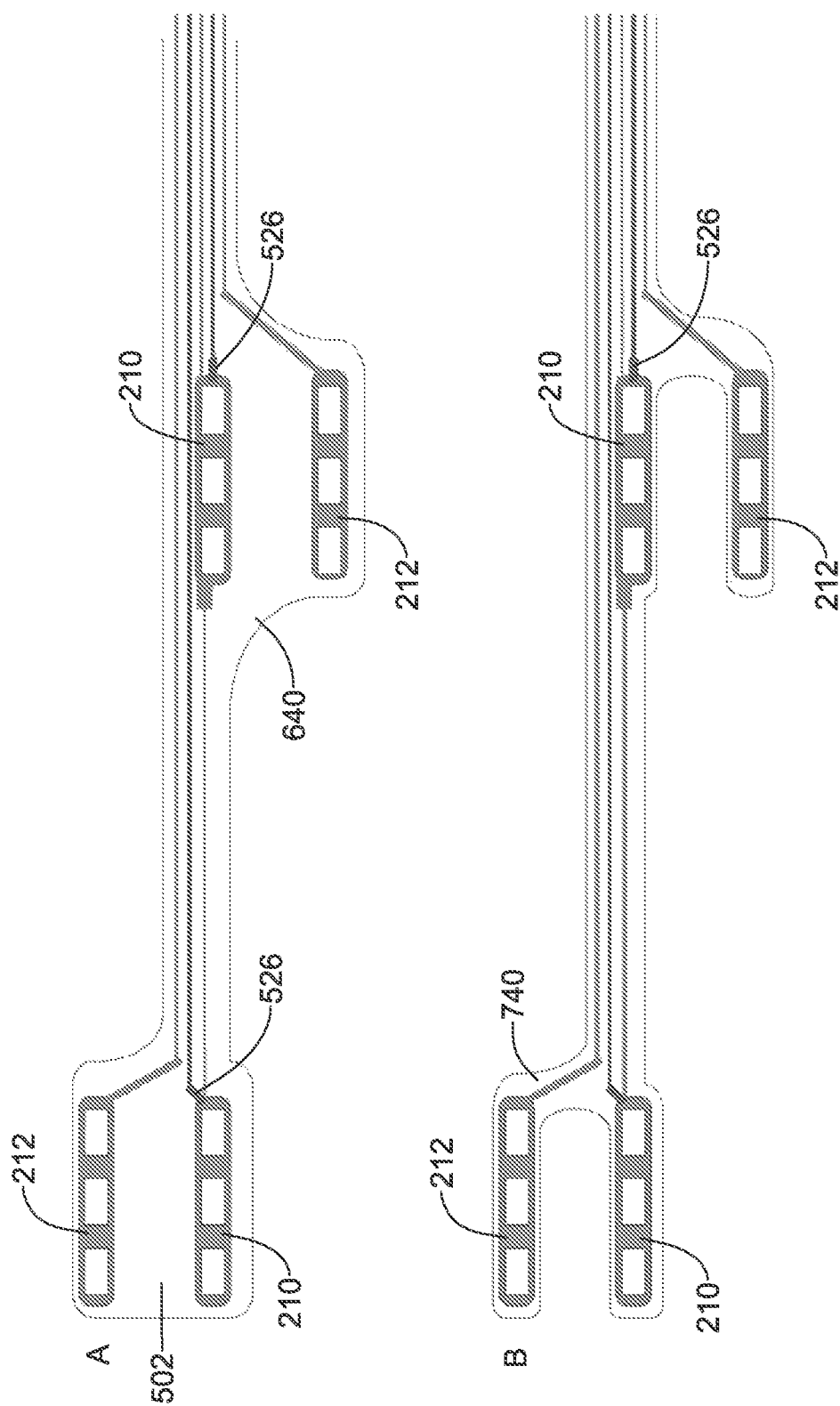

As shown in FIG. 6B, the ground electrode trace 210 and active electrode trace 212 may each include a plurality of electrodes 222. In some embodiments, at least one electrode may be provided for each electrode trace, however, more or less may be used. For example, in some embodiments, three electrodes may be provided for each electrode trace. See FIGS. 11-13. In other embodiments, up to 35 or more electrodes may be provided for each electrode trace, as shown in FIGS. 7 and 8. The plurality of electrodes 222 may protrude above and/or extend through the insulating layer 206. In some embodiments, the plurality of electrodes 222 may include at least one active electrode and at least one ground electrode attached and/or electrically connected to the elongated active electrode support 217 and the elongated ground electrode support 216, respectively. In some embodiments, a plurality of electrodes 222 may be attached and/or electrically connected to the elongated ground electrode support 216, thereby defining a plurality of ground electrodes, and/or the elongated active electrode support 217, thereby defining a plurality of active electrodes.

In some embodiments, the plurality of electrodes 222 may be from about 0.030 mm thick to about 0.070 mm thick. In some embodiments, the plurality of electrodes 222 may be about 0.051 mm thick. In some embodiments, the plurality of electrodes 222 may extend about 0.020 mm to about 0.050 mm above the insulating layer 206. In some embodiments, the plurality of electrodes 222 may extend about 0.038 mm above the insulating layer 206. Additionally, each electrode may have radiused corners to reduce tendency to snag on other devices and/or tissue. Although the above description of the plurality of electrodes and the traces associated with them has been described in the context of a bi-polar electrode assembly, those of skill in the art will recognize that the same electrode assembly may function in a monopolar mode as well. For instance, as one non-limiting example, the plurality of electrodes associated with active electrode trace 212 may be used as monopolar electrodes, with ground electrode trace 210 disconnected during energization of those electrodes.

In some embodiments, the temperature sensor 226 may have a length of about 0.100 mm to about 2.000 mm, and a width of about 0.100 mm to about 0.800 mm. In some embodiments, the temperature sensor 226 may have a length of about 1.000 mm and a width of about 0.500 mm. In another embodiment, the temperature sensor may have a length of about 0.2 mm and a width of 0.01 mm. Other sizes and/or dimensions are contemplated.

In some embodiments the electrodes may be canted around the balloon at a slight angle to form a helical configuration around the balloon, which may aid in retraction of the balloon after treatment. For example, as shown in FIG. 7, a plurality of electrode assemblies 140 may be positioned at an angle on the expandable member 130, shown in an expanded state. The electrode assemblies 140 may be configured such that energy applied by the electrode assemblies create treatments that may or may not overlap. Treatments applied by the electrode assemblies 140 may be circumferentially continuous or non-continuous along longitudinal axis L-L. The energy applied by the electrode assemblies, such as the electrode assemblies 140 shown in FIG. 7, may overlap, longitudinally, circumferentially, and/or in other ways, to at least some extent. The electrode assembly 140 shown in FIGS. 7 and 8 may include a base layer 202 in a rectangular shape. This is not intended to be limiting. Other shapes are contemplated. Additionally, the electrode assembly 140 may include a plurality of openings extending therethrough to provide for added flexibility, and the portions of the assemblies may include rounded or curved corners, transitions and other portions. In some instances, the openings and rounded/curved features may enhance the assembly's resistance to delamination from the expandable member 130, as may occur, in some instances, when the expandable member 130 is repeatedly expanded and collapsed (which may also entail deployment from and withdrawal into a protective sheath), such as may be needed when multiple sites are treated during a procedure.

One example electrode assembly 140 is illustrated in FIG. 8. As shown in FIG. 8, each electrode assembly 140 may include one or more temperature sensor 226 on a sensor trace 214, a plurality of electrodes 222, some disposed on a ground array or trace 210 and some disposed on an active or positive array or trace 212. The sensor trace 214 may be centrally located on the electrode assembly 140. In other examples, the sensor trace 214 may be located adjacent one of the arrays or traces 210, 212. Each electrode assembly 140 includes a proximal tail 180 which may include a narrowed region extending off the proximal end of the expandable member 130 and along the catheter shaft 122 to a proximal end of the catheter shaft 122.

Figure 9:
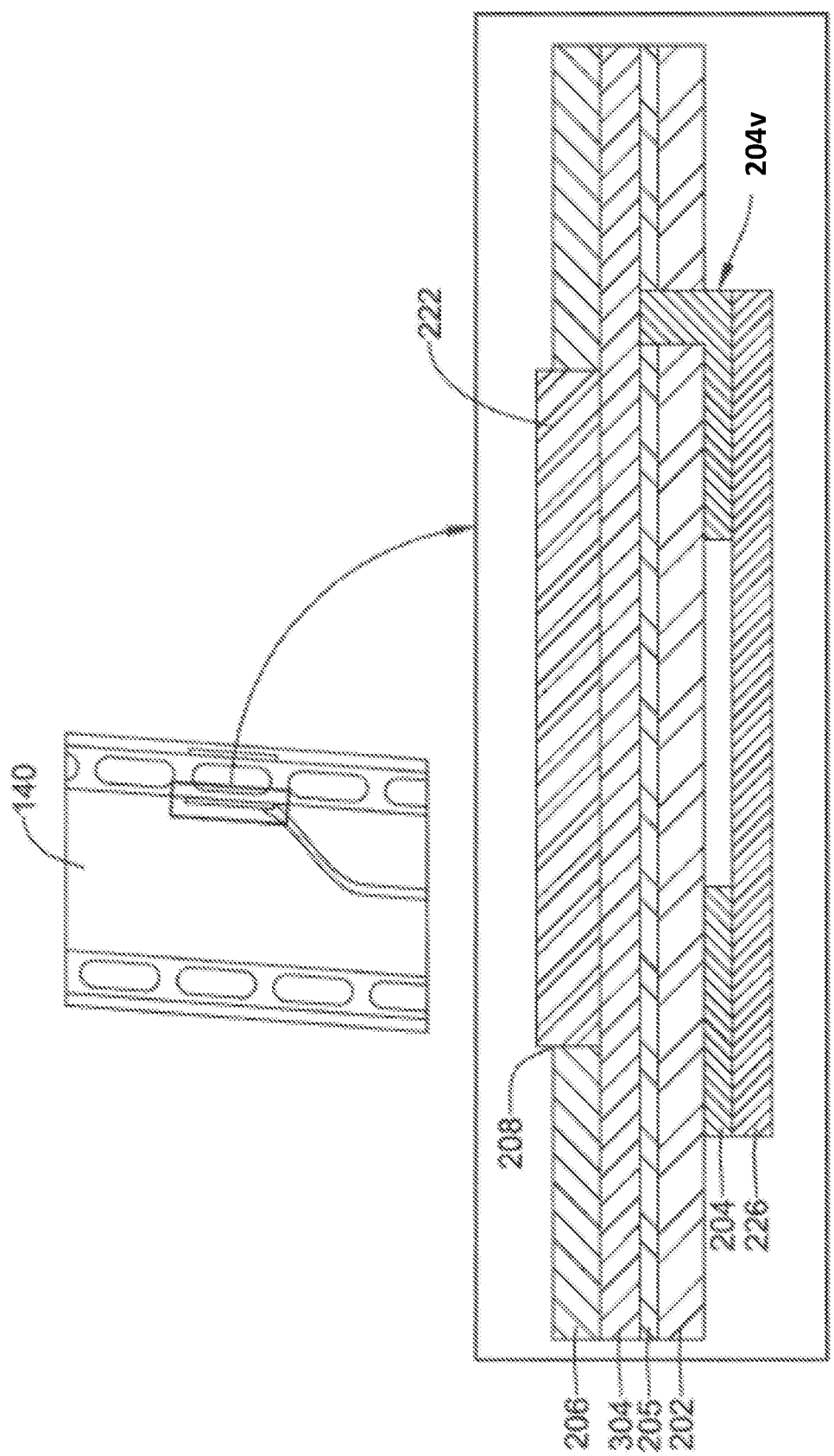
FIG. 9 is a partial cross-sectional view of FIG. 8.

In some embodiments, the temperature sensor 226 may be a thermistor. As shown in FIG. 9, the temperature sensor 226 may be disposed on a non-tissue contacting side (i.e., bottom side) of the electrode assembly 140. Accordingly, the temperature sensor 226 may be captured between the electrode assembly 140 and the expandable member 130 when incorporated into an ablation device 120. This may be advantageous since surface-mounted electrical components, like thermistors, may typically have sharp edges and corners, which may get caught on tissue and possibly cause problems in balloon deployment and/or retraction. This arrangement may also keep soldered connections from making contact with blood, since solder is typically non-biocompatible.

The size and/or thickness of the electrode assembly 140 at the temperature sensor 226 may create a protrusion extending outward from the outer surface of the expandable member 130. Following a treatment procedure, the expandable member 130 may be collapsed to a collapsed delivery configuration, as discussed further herein, and the ablation device 120 may be retracted within the guide sheath or catheter 14. Significant protrusion(s) may make retraction into the guide sheath or catheter 14 more difficult and/or require a larger diameter guide sheath or catheter 14 than would otherwise be desired. Additionally, the protrusion(s) may negatively impact the foldability characteristics of the expandable member 130, both for delivery and for withdrawal.

FIG. 9 shows a partial top view of an example electrode assembly 140 and a cross section thereof. In the cross-sectional view of FIG. 9, the bottom of the figure is the portion of the electrode assembly 140 that may face, may be in contact with, and/or may be attached and/or bonded directly to an outer surface of the expandable member 130. In some embodiments, a base layer 202 of insulation which may provide a foundation for the electrode assembly 140. The base layer 202 may be constructed from a polymer such as polyimide, although other materials are contemplated. In some embodiments, the base layer 202 may be about 0.010 mm to about 0.020 mm thick. In some embodiments, the base layer 202 may be about 0.015 mm thick. Other suitable thicknesses are also contemplated. For reference, the base layer 202 may form the majority of the bottom side of the electrode assembly 140 that may face, may be in contact with, and/or may be attached and/or bonded directly to the outer surface of the expandable member 130.

A first conductive layer 204 may include a plurality of discrete conductive traces layered on the base layer 202. In some embodiments, the plurality of discrete conductive traces may be separated laterally by a non-conductive material. The plurality of discrete conductive traces of the conductive layer 204 may include, for example, a layer of electrodeposited copper or rolled-annealed copper. Other suitable conductive materials are also contemplated. In some embodiments, the conductive layer 204 and/or the plurality of discrete conductive traces may be about 0.010 mm to about 0.030 mm thick. In some embodiments, the conductive layer 204 and/or the plurality of discrete conductive traces may be about 0.018 mm thick. Other suitable thicknesses are also contemplated. The first conductive layer 204 may be etched to form the positive and ground connection for the temperature sensor 226, which may be placed over the first conductive layer.

A second conductive layer 304 may be disposed over the base layer 202, and an insulating layer 206 may be discretely or continuously layered on top of the second conductive layer 304, such that the second conductive layer 304 may be fluidly sealed between the base layer 202 and the insulating layer 206. In other words, the insulating layer 206 may form a top side or surface of the electrode assembly 140 that may face away from the outer surface of the expandable member 130. The relationship between the base layer 202, the first conductive layer 204, the second conductive layer 304, and the insulating layer 206 is illustrative, and other constructions are contemplated. Like the base layer 202, the insulating layer 206 may be constructed from a polymer such as polyimide, although other materials are contemplated. In some embodiments, the insulating layer 206 may be from about 0.010 mm thick to about 0.020 mm thick. In some embodiments, the insulating layer 206 may be about 0.013 mm thick. Other suitable thicknesses are also contemplated. In some embodiments, the insulating layer 206 may be a complete or partial polymer coating, such as PTFE or silicone. Other materials are also contemplated.

The electrode assembly 140 may be constructed as a flexible circuit having a plurality of layers. Such layers may be continuous or non-contiguous (i.e., made up of discrete portions). The electrode assembly 140 may be a multiple layer structure with an electrode 222 on an upper surface (away from the expandable member) and a temperature sensor such as a temperature sensor 226 on a lower surface (against the expandable member). The electrode assembly 140 may include one or more layers of polymer and one or more layers of a conductive material. As shown in cross-section in FIG. 9, the electrode assembly 140 may include two polymer layers 202, 206, two conductive layers 204, 304, a temperature sensor 226, and an electrode 222. The polymer and conductive layers may be laminated sheets of a polymer layer 202, 206 adhesively bonded to a conductive layer 204, 304. In some embodiments, two such sheets may be bonded together with an adhesive layer 205. As shown in FIG. 9, two polymer/conductive sheets may be bonded together with a polymer side against a conductive side, resulting in an alternating polymer 206-conductive 304-adhesive 205-polymer 202-conductive 204 structure, when a cross-section is taken starting with the upper surface (away from the expandable member).

The second conductive layer 304 may be etched to form traces for the ground and positive electrode 222 pairs. A via 204v may be created to connect the electrode ground trace of the second conductive layer 304 to the temperature sensor 226 and ground trace of the first conductive layer 204. The temperature sensor 226 may be soldered onto the first conductive layer 204. The insulation layer 206 may be skived to form a recess 208 to allow for gold plating to form gold electrodes 222.

Figure 10A:
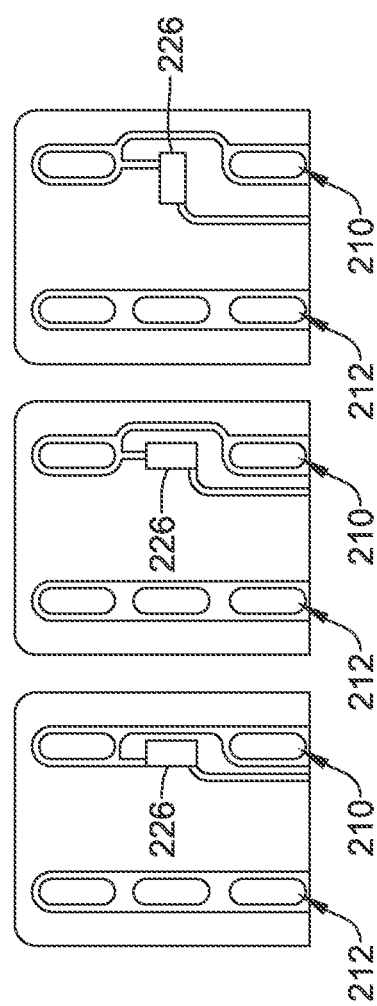

In other embodiments, shown in FIG. 10A, one of the ground electrode recesses may be removed and the temperature sensor 226 may be positioned in the region where the recess would have been. The recess 208 may be oriented in any direction. The first conductive layer 204 may be designed to share the ground trace 210 with the temperature sensor 226 while a new trace may be formed for the positive connection of the temperature sensor. For longer electrodes that may require more temperature sensors, the temperature sensors may be positioned along the ground trace 210 and may be wired in parallel with each other as shown in FIG. 10B. Alternatively, when multiple temperature sensors are used, they may be wired separately (not shown).

In some embodiments, the electrode assembly(s) 140 may be disposed along or otherwise define pre-determined fold lines along which the expandable member 130 may fold after deflation. In some embodiments, the pre-determined fold lines may aid in re-folding of the expandable member 130. In some embodiments, the electrode assembly(s) 140 may be substantially linear, extending along or at an angle to the longitudinal axis L-L along the entire length of the expandable member 130. In some embodiments, the electrode assemblies may extend parallel to the longitudinal axis in a proximal region, and then be bent into an angled orientation in a distal region (not shown). The electrode assembly(s) 140 may cause the balloon to fold along the lines of the electrode assembly(s) 140, reducing the withdrawal force needed to withdraw the ablation device 120 into the guide sheath or catheter 14, and allowing the use of a smaller diameter guide sheath. For example, a 6 Fr or 7 Fr guide catheter 14 may be used, providing advantages in certain procedures, (e.g., renal procedures), where 8 Fr guide catheters have been previously used. The electrode assembly(s) 140 may also reduce shear force or improve balloon refold profile efficiency, thereby reducing delamination of the electrode assembly(s) 140 from the expandable member 130.

In some embodiments, the electrode assemblies 140 include a single row or array of positive electrodes 212 and a single row or array of ground electrodes 210, as shown in FIG. 8. In other embodiments, the electrode assemblies 340, 440 may include longitudinally spaced apart electrode pads 308, 336 and 408, 436, as shown in FIGS. 11A and 11B. Moving proximally from the distal electrode pad 308, 408, the combined base layer 202, conductive layer 304, and insulating layer 206 may reduce in lateral width to an intermediate tail 328, 428. Continuing to move proximally from the intermediate tail 328, 428, the combined base layer 202, conductive layer 304, and insulating layer 206 may increase in lateral width to form a proximal electrode pad 336, 436. The proximal electrode pad 336, 436 may be constructed similarly to the distal electrode pad 308, 408. However, as shown, the proximal electrode pad 336, 436 may be laterally offset from the distal electrode pad 308, 408 with respect to a central longitudinal axis extending along the electrode assembly 340, 440.

From the proximal electrode pad 336, 436, the combined base layer 202, conductive layer 304, and insulating layer 206 may reduce in lateral width to form a proximal tail 338, 438. The proximal tail 338, 438 may include connectors (not shown) to enable coupling to one or more sub-wiring harnesses and/or connectors and ultimately to control unit 110. Each of these lines may be extended along parallel respective axes with respect to the central axis of the electrode assembly 340, 440.

The electrode assembly 340, 440 may have a symmetric or an asymmetric arrangement of the distal electrode pad 308, 408 and proximal electrode pad 336, 436, about the central axis of the electrode assembly 340, 440. Further, the ground electrodes 210 of both electrode pads may be substantially aligned along the central axis, along with the ground lines. It has been found that this arrangement may present certain advantages. For example, by essentially sharing the same ground trace, the width of the proximal tail may be only about one and a half times that of the intermediate tail, rather than being approximately twice as wide if each electrode pad had independent ground lines. Thus, the proximal tail 338, 438 may be narrower than two intermediate tails 328, 428 positioned side-by-side.

FIG. 11A illustrates an electrode assembly 340 with linear rows of positive electrodes 212 and ground electrodes 210, where substrate material, including a base layer 202, extends between the rows. FIG. 11B illustrates a similar electrode assembly 440 with the substrate material cut out between the linear rows of electrodes 212, 210. The removal of substrate material between the rows of electrodes reduces the mass of the circuit that must be folded. When disposed on a balloon, the electrode assembly 440 may provide enhanced foldability as compared to electrode assembly 340 because lack of substrate between the linear rows of electrodes may allow for easier folding between the electrode rows, with the temperature sensor 226 being folded with the ground electrodes 210. This structure may allow the device to be inserted and withdrawn through a smaller sheath or catheter. However, even with the base layer 202 present between the rows of electrodes, as shown in FIG. 11A, moving the temperature sensor 226 away from the center and onto a row of electrodes provides enhanced foldability over the prior art electrode assemblies shown in FIGS. 2A and 2B. The electrode assemblies 340, 440 shown in FIGS. 11A and 11B also show a temperature sensor 226 placed in line with and proximal of the most proximal ground electrode 210. This configuration provides the electrodes and temperature sensors in two linear rows, which may aid in folding the electrode assembly along a line between the rows of electrodes.

In some embodiments, the temperature sensor 226 may be a sputtered thermocouple (for example, Type T configuration: Copper/Constantan). In the embodiment illustrated in FIGS. 12A and 12B, the temperature sensor is a thermocouple 426 with a junction close to the middle electrode on the ground trace 210. The middle electrode may have less variation due to apposition of the balloon and may have better correlation or error to the prior art center position. In some embodiments, the thermocouple may include separate layers of copper and constantan. The thermocouple can be formed by a through hole between the two layers and may be filled with solder, which makes the through hole the thermocouple junction. As in FIGS. 11A and 11B, FIG. 12A shows an electrode assembly 440 with substrate or base layer 402 disposed between the ground trace 210 and the positive trace 212, while FIG. 12B shows an electrode assembly 540 with the substrate removed between the rows of positive and negative electrodes.

The thermocouple junction may be placed on or near a proximal ground electrode, as shown in FIGS. 13A and 13B. The thermal junction may be made of copper and constantan (T-type), instead of gold and constantan. However, the junction is close to the copper layer so it can measure the exact temperature of the heating element. A thermocouple may generate a voltage differential at the junction of two dissimilar metals based upon the temperature at the junction, as is known in the art. In some embodiments, an isothermal junction may be formed at a proximal end of the electrode assembly 140, spaced apart from and thermally isolated from the electrode pad(s) and/or the plurality of electrodes. In some embodiments, the temperature sensor 226 may be formed as a discrete trace of electrodeposited copper within the conductive layer 204. In some embodiments, the distal end portion of the sensor trace 214, and in some cases the entire sensor trace 214 may be formed from, for example, constantan (i.e., copper-nickel alloy), nickel-chromium, or other suitable conductive material.

FIG. 13A shows another embodiment of electrode assembly 640 having parallel rows of ground electrodes 210 and positive electrodes 212 on a substrate or base layer 502. The temperature sensor 526 may be a thermocouple with a junction at the proximal end of the proximal-most ground electrode 210. FIG. 13B shows a similar electrode assembly 740 with a portion of the base layer 502 removed between the rows of ground electrodes 210 and positive electrodes 212.

Figure 14:
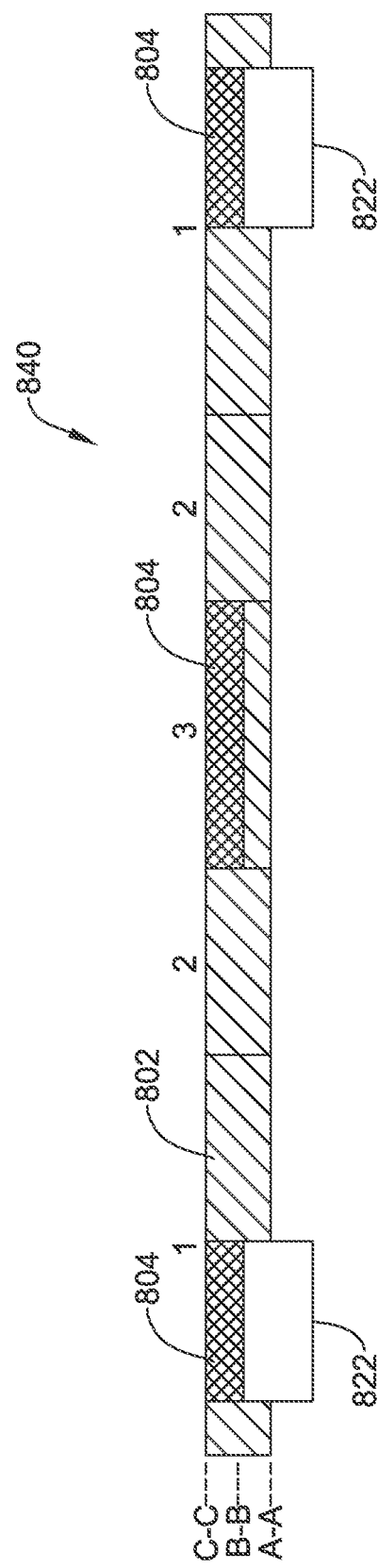
FIG. 14 is a partial cross-sectional view of an exemplary electrode assembly.

Exemplary devices have a very uniform temperature profile on the balloon and inside tissue during RF delivery due to their balloon structure and bipolar energy delivery. FIG. 14 is a cross-sectional view of a simplified model electrode assembly 840 with electrodes 822, conductive layer 804, and base layer or substrate 802. FIGS. 15A-15C show thermal profiles of various surfaces at 30 seconds of heating. FIG. 15A shows the surface of polyimide base layer 802, through section A-A in FIG. 14. FIG. 15B shows the interface between a copper conductive layer 804 and the polyimide base layer 802, through section B-B in FIG. 14. FIG. 15C shows the balloon outer diameter at section C-C in FIG. 14. As can be seen when comparing FIGS. 15A-15C, the temperature profile is essentially constant across the cross-section of the electrode assembly 840. The temperature at the center of the balloon 1501 is close to the temperature at the electrodes 1502. Because of this consistency, the temperature at the center of the balloon 1501 is also close to and well correlated with the temperature at the edge of the electrode assembly 1502.

Figure 16:
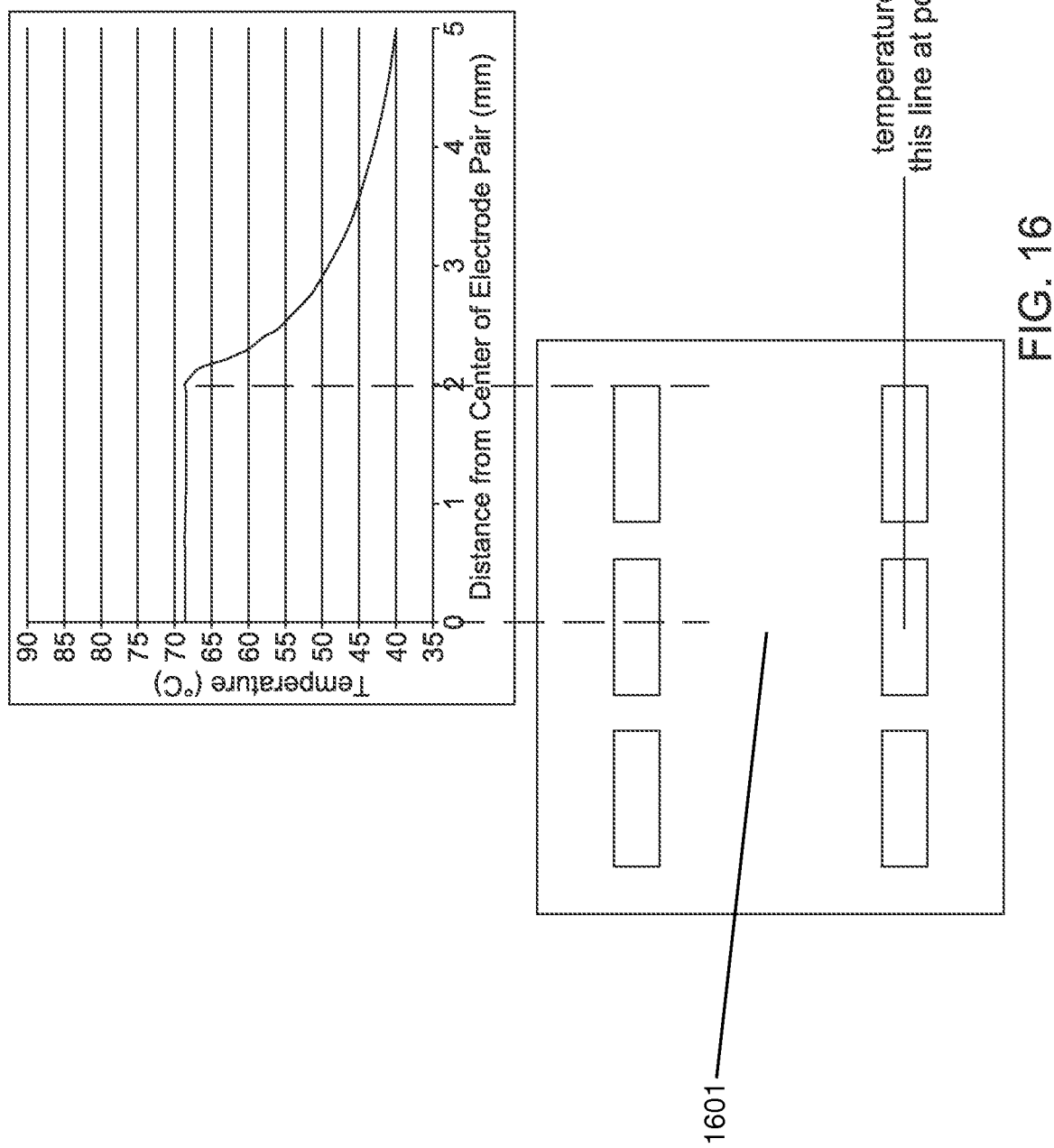
FIG. 16 is a graphical representation of the temperature profile at varying distances from the center of an exemplary electrode.

FIG. 16 illustrates the temperature at the center of an electrode pair 1601 and at various distances from the center. As can be seen, the temperature is essentially constant from the center of the electrode pair to the edge of the row of electrodes. A temperature measurement near an electrode has been found to be suitable for temperature control instead of a center temperature measurement, while maintaining lesion consistency.

In use, the ablation device 120 may be advanced through a blood vessel or body passageway to a position adjacent to a target tissue (e.g., within a renal artery), in some cases with the aid of a delivery sheath or catheter 14. In some embodiments, the target tissue may be one or more sympathetic nerves disposed about the blood vessel. In some embodiments, the control unit 110 may be operationally coupled to the ablation device 120, which may be inserted into a blood vessel or body passageway such that an expandable member 130 (having a plurality of electrode assemblies 300) may be placed adjacent to the target tissue where therapy is required. Placement of the ablation device 120 adjacent the target tissue where therapy is required may be performed according to conventional methods, (e.g., over a guidewire under fluoroscopic guidance). When suitably positioned, the expandable member 130 may be expanded from a collapsed delivery configuration to an expanded configuration, for example by pressurizing fluid from about 2-10 atm in the case of a balloon. This may place/urge the plurality of electrodes against the wall of the blood vessel. The plurality of active electrodes may be activated. Ablation energy may be transmitted from the plurality of active electrodes through the target tissue (where sympathetic nerves may be ablated, modulated, or otherwise impacted), and back through the plurality of ground electrodes, in a bipolar configuration, or back through the common ground electrode, in a monopolar configuration. Following treatment, the expandable member 130 may be collapsed to the collapsed delivery configuration for retraction into the guide sheath or catheter 14 and subsequent withdrawal from the blood vessel or body passageway.

The materials that can be used for the various components of the ablation device 120 (and/or other devices disclosed herein) may include those commonly associated with medical devices. For simplicity purposes, the following discussion makes reference to the ablation device 120. However, this is not intended to limit the devices and methods described herein, as the discussion may be applied to other similar tubular members and/or expandable members and/or components of tubular members and/or expandable members disclosed herein.

The ablation device 120 and the various components thereof may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304 L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear that the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also can be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Some examples of nickel titanium alloys are disclosed in U.S. Pat. Nos. 5,238,004 and 6,508,803, which are incorporated herein by reference. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions of the ablation device 120 may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the ablation device 120 in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the ablation device 120 to achieve the same result.

In some embodiments, a degree of Magnetic Resonance Imaging (MRI) compatibility may be imparted into the ablation device 120. For example, portions of device, may be made of a material that does not substantially distort the image and create substantial artifacts (i.e., gaps in the image). Certain ferromagnetic materials, for example, may not be suitable because they may create artifacts in an MRI image. In some of these and in other embodiments, portions of the ablation device 120 may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

U.S. patent application Ser. No. 13/750,879, filed on Jan. 25, 2013, now U.S. Patent Publication No. US20130165926A1 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. A method of applying thermal energy to tissue, comprising:
   inserting an expandable member having a plurality of pairs of electrodes, each pair comprising an active electrode, a ground electrode and one or more temperature sensors associated therewith, within a patient; wherein the plurality of pairs of electrodes and the one or more temperature sensors are positioned on a multiple-layer structure comprising a first laminated sheet including a first polymer layer laminated to a first conductive layer and a second laminated sheet including a second polymer layer laminated to a second conductive layer; wherein the one or more temperature sensors are in contact with the first conductive layer; wherein the plurality of pairs of electrodes are in contact with the second conductive layer; wherein the first conductive layer forms a positive trace and a ground trace for the one or more temperature sensors; and wherein the second conductive layer forms a positive trace and a ground trace for the plurality of pairs of electrodes;
   expanding the expandable member to an expanded state;
   activating the plurality of pairs of electrodes; and
   monitoring the temperature between the plurality of pairs of electrodes by measuring a temperature from each of the one or more temperature sensors.

2. The method of claim 1, wherein the one or more temperature sensors comprise one or more thermistors.

3. The method of claim 2, wherein at least one thermistor of the one or more thermistors is disposed between each pair of the plurality of pairs of electrodes, and further comprising monitoring the temperature within each pair of electrodes by measuring a temperature from the at least one thermistor of the one or more thermistors disposed therebetween.

4. The method of claim 1, where the expandable member is coupled to a catheter shaft, and the expandable member is capable of being shifted between the expanded state and an unexpanded state along pre-determined fold lines of the expandable member.

5. The method of claim 4, wherein inserting the expandable member is performed in the unexpanded state with the expandable member folded at least between the plurality of pairs of electrodes along the fold lines.

6. The method of claim 1, wherein one or more pairs of the plurality of pairs of electrodes are arranged on one or more elongate electrode assemblies, each assembly constructed as a flexible circuit, the assemblies disposed on an outer surface of the expandable member.

7. The method of claim 1, wherein the one or more temperature sensors and the plurality of pairs of electrodes are arranged on a plurality of electrode pads.

8. The method of claim 1, wherein the pairs of electrodes are arranged side-by-side and longitudinally along the expandable member.

9. A method of applying thermal energy to tissue, comprising:
inserting an expandable member of a device within a patient, the device further comprising a plurality of pairs of electrodes, each comprising an active electrode and a ground electrode, constructed as a flexible circuit disposed on an outer surface of the expandable member and having one or more temperature sensors associated therewith; wherein the plurality of pairs of electrodes and the one or more temperature sensors are positioned adjacent to a multiple-layer structure comprising a first laminated sheet including a first polymer layer laminated to a first conductive layer and a second laminated sheet including a second polymer layer laminated to a second conductive layer; wherein the one or more temperature sensors are in contact with the first conductive layer; wherein the plurality of pairs of electrodes are in contact with the second conductive layer; wherein the first conductive layer forms a positive trace and a ground trace for the one or more temperature sensors; and wherein the second conductive layer forms a positive trace and a ground trace for the plurality of pairs of electrodes;
expanding the expandable member to an expanded state;
activating the plurality of pairs of electrodes; and
monitoring the temperature between the plurality of pairs of electrodes by measuring a temperature from each of the one or more temperature sensors positioned between the plurality of pairs of electrodes.

10. The method of claim 9, wherein the one or more temperature sensors comprise one or more thermistors.

11. The method of claim 10, wherein at least one thermistor of the one or more thermistors is disposed between each pair of the plurality of pairs of electrodes, and further comprising monitoring the temperature within each pair of electrodes by measuring a temperature from the at least one thermistor of the one or more thermistors disposed therebetween.

12. The method of claim 9, wherein the pairs of electrodes are arranged side-by-side and longitudinally along the expandable member.

13. The method of claim 9, wherein inserting the expandable member is performed in an unexpanded state with the expandable member folded at least between the pairs of electrodes.

14. The method of claim 9, wherein the one or more temperature sensors and the plurality of pairs of electrodes are arranged on a plurality of electrode pads.

15. A method of applying thermal energy to tissue, comprising:
inserting an expandable member of a device within a patient, the device further comprising a plurality of pairs of electrodes disposed on an outer surface of the expandable member, each pair of the plurality of pairs of electrodes comprising an active electrode, a ground electrode, and one or more temperature sensors associated therewith; wherein the plurality of pairs of electrodes and the one or more temperature sensors are positioned adjacent to a multiple-layer structure comprising a first laminated sheet including a first polymer layer laminated to a first conductive layer and a second laminated sheet including a second polymer layer laminated to a second conductive layer; wherein the one or more temperature sensors are in contact with the first conductive layer; wherein the plurality of pairs of electrodes are in contact with the second conductive layer; wherein the first conductive layer forms a positive trace and a ground trace for the one or more temperature sensors; and wherein the second conductive layer forms a positive trace and a ground trace for the plurality of pairs of electrodes;
expanding the expandable member to an expanded state;
activating the plurality of pairs of electrodes; and
monitoring the temperature between the plurality of pairs of electrodes by measuring a temperature from each of the one or more temperature sensors.

16. The method of claim 15, wherein the one or more temperature sensors comprise one or more thermistors.

17. The method of claim 16, wherein at least one thermistor of the one or more thermistors is disposed between each pair of the plurality of pairs of electrodes, and further comprising monitoring the temperature within each pair of electrodes by measuring a temperature from the at least one thermistor of the one or more thermistors disposed therebetween.

18. The method of claim 15, wherein the pairs of electrodes are arranged side-by-side and longitudinally along the expandable member.

19. The method of claim 15, wherein inserting the expandable member is performed in an unexpanded state with the expandable member folded at least between the pairs of electrodes.

20. The method of claim 15, wherein one or more pairs of the plurality of pairs of electrodes are arranged on one or more elongate electrode assemblies, each assembly constructed as a flexible circuit, the assemblies disposed on the outer surface of the expandable member.

* * * * *